US00PP25702P2

(12) United States Plant Patent
Kapusta

(10) Patent No.: US PP25,702 P2
(45) Date of Patent: Jul. 14, 2015

(54) ***LONICERA* PLANT NAMED 'INOV205'**

(50) Latin Name: *Lonicera periclymenum*
Varietal Denomination: Inov205

(71) Applicant: Veronique Kapusta, Beaucouze (FR)

(72) Inventor: Veronique Kapusta, Beaucouze (FR)

(73) Assignees: Institut National de la Recherche Agronomique, Paris (FR); Saphinov S.N.C., Beaufort En Vallee (FR)

( * ) Notice: Subject to any disclaimer, the term of this patent is extended or adjusted under 35 U.S.C. 154(b) by 85 days.

(21) Appl. No.: 13/987,776

(22) Filed: Aug. 31, 2013

(51) Int. Cl.
*A01H 5/00* (2006.01)

(52) U.S. Cl.
USPC ..... Plt./226

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Lonicera* plant named 'Inov205', characterized by its compact plant habit; freely flowering habit; long flowering period; relatively large inflorescences; purple-colored flower buds; light pink and yellow-colored flowers; and good garden performance and winter hardiness.

3 Drawing Sheets

Botanical designation: *Lonicera periclymenum.*
Cultivar denomination: 'INOV205'.

BACKGROUND OF THE INVENTION

The present invention relates to a new and distinct cultivar of *Lonicera* plant, botanically known as *Lonicera periclymenum*, commonly referred to as Honeysuckle and hereinafter referred to by the name 'Inov205'.

The new *Lonicera* is a product of a planned breeding program conducted by the Inventor in Beaucouzé, France. The objective of the breeding program was to develop new compact and freely flowering *Lonicera* plants with large and attractive flowers.

The new *Lonicera* plant originated from a self-pollination in 2003 of a proprietary seedling of *Lonicera periclymenum* identified as code number L137, not patented. The new *Lonicera* plant was discovered and selected by the Inventor in 2005 as a single flowering plant within the progeny of the stated self-pollination in a controlled environment in Beaucouzé, France.

Asexual reproduction of the new *Lonicera* plant by softwood cuttings in a controlled greenhouse environment in La Ménitré, Maine et Loire, France since 2008 has shown that the unique features of this new *Lonicera* plant are stable and reproduced true to type in successive generations of asexual reproduction.

SUMMARY OF THE INVENTION

Plants of the new *Lonicera* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Inov205'. These characteristics in combination distinguish 'Inov205' as a new and distinct *Lonicera* plant:

1. Compact plant habit.
2. Freely flowering habit and long flowering period.
3. Relatively large inflorescences.
4. Purple-colored flower buds.
5. Light pink and yellow-colored flowers.
6. Good garden performance and winter hardiness.

Plants of the new *Lonicera* can be compared to plants of the parent selection. In side-by-side comparisons, plants of the new *Lonicera* differ primarily from plants of the parent selection in the following characteristics:

1. Plants of the new *Lonicera* are more compact than plants of the parent selection.
2. Plants of the new *Lonicera* are not as vigorous as plants of the parent selection.
3. Plants of the new *Lonicera* are more stable and uniform than plants of the parent selection.

Plants of the new *Lonicera* can be compared to plants of *Lonicera periclymenum* 'Inov71', disclosed in U.S. Plant Pat. No. 21,874. In side-by-side comparisons plants of the new *Lonicera* differed primarily from plants of 'Inov71' in plant habit and flower color.

BRIEF DESCRIPTION OF THE PHOTOGRAPHS

The accompanying colored photographs illustrate the overall appearance of the new *Lonicera* plant showing the colors as true as it is reasonably possible to obtain in colored reproductions of this type. Colors in the photographs may differ slightly from the color values cited in the detailed botanical description which accurately describe the colors of the new *Lonicera* plant.

The photograph on the first sheet is a side perspective view of a typical flowering plant of 'Inov205' grown in a container.

The photograph on the second sheet is a close-up view of a typical leaf of 'Inov205'.

The photograph on the third sheet is a close-up view of a typical inflorescence of 'Inov205'.

DETAILED BOTANICAL DESCRIPTION

The aforementioned photographs and following observations, measurements and values describe plants grown in 13-cm containers during the summer in an outdoor nursery in La Ménitré, Maine et Loire, France and under cultural practices which closely approximate commercial *Lonicera* production. During the production of the plants, day temperatures ranged from 20° C. to 32° C. and night temperatures ranged from 12° C. to 20° C. Plants were one year old when the photographs and the description were taken. In the description, color references are made to The Royal Horticultural Society Colour Chart, 2007 Edition, except where general terms of ordinary dictionary significance are used.

Botanical classification: *Lonicera periclymenum* 'Inov205'.

Parentage: Self-pollination of a proprietary seedling of *Lonicera periclymenum* identified as code number L137, not patented.

Propagation:

*Type*.—By softwood cuttings.

*Time to initiate roots, summer*.—About one month at 25° C.

*Root description*.—Fine; white in color.

*Rooting habit*.—Moderate branching; medium density.

Plant description:

*Plant form and growth habit*.—Perennial deciduous shrub; compact plant habit; broad inverted triangle; low to moderate vigorous growth habit.

*Branching habit*.—Moderately freely branching habit; pinching enhances lateral branch development.

*Plant height*.—About 21 cm.

*Plant diameter* (*area of spread*).—About 23 cm.

Lateral branch description:

*Length*.—About 5.9 cm.

*Diameter*.—About 2.5 mm.

*Internode length*.—About 1.8 cm.

*Strength*.—Strong, sturdy.

*Texture*.—Smooth, glabrous; waxy.

*Color*.—Close to N186C; waxy layer, close to N187D.

Leaf description:

*Arrangement*.—Opposite, simple.

*Length*.—About 4.8 cm.

*Width*.—About 2.4 cm.

*Shape*.—Ovate to elliptic.

*Apex*.—Bluntly acute to obtuse.

*Base*.—Obtuse.

*Margin*.—Entire; slightly undulate.

*Texture, upper and lower surfaces*.—Smooth, glabrous.

*Venation pattern*.—Pinnate.

*Color*.—Developing leaves, upper surface: Close to 143A strongly tinged with close to 200A to 200B. Developing leaves, lower surface: Close to N200B. Fully expanded leaves, upper surface: Close to N137A to N137B; venation, close to 145A. Fully expanded leaves, lower surface: Close to 138B; venation, close to 146C tinged with close to 176C.

*Petioles*.—Length: About 1.5 mm. Diameter, flattened: About 2 mm. Height: About 1 mm. Texture, upper and lower surfaces: Smooth, glabrous. Color, upper surface: Close to 145A. Color, lower surface: Close to 176C.

Flower description:

*Flower appearance and arrangement*.—Narrowly campanulate flowers arranged on terminal verticillasters; freely flowering habit with about 35 flowers developing per inflorescence; flowers face mostly outwardly; flowers sessile.

*Inflorescence height*.—About 5.2 cm.

*Inflorescence width*.—About 8.4 cm.

*Fragrance*.—Moderately fragrant; sweet, pleasant.

*Natural flowering season*.—Long flowering period, plants flower continuously from early to late summer in France.

*Flower longevity*.—Flowers last about one week on the plant; flowers not persistent.

*Flower diameter*.—About 1.7 cm.

*Flower height*.—About 3.2 cm.

*Flower depth*.—About 4.3 cm.

*Flower buds*.—Length: About 2.5 cm. Diameter: About 5 mm. Shape: Oblanceolate, curved upwards. Color: Close to 187D.

*Petals*.—Quantity and arrangement: Bilabiate flowers with a four-lobed upper lip and single-lobed lower lip. Lobe length: About 4.5 cm. Lobe width: About 4.5 mm. Shape: Narrowly oblanceolate. Apex: Obtuse. Margin: Entire. Texture, upper and lower surfaces: Smooth, glabrous. Color: When opening, upper surface: Close to 160D tinged with close to 186C. When opening, lower surface: Close to 186B; towards the margins, close to between 155A and 160D; tube, close to 186C to 186D. Fully opened, upper surface: Close to 160D tinged with close to 186C; color becoming closer to 162A with development. Fully opened, lower surface: Close to 186B; towards the margins, close to between 155A and 160D; tube, close to 186C to 186D.

*Sepals*.—Quantity and arrangement: Five in a single whorl. Length: About 1 mm. Width: About 1 mm. Shape: Deltoid. Apex: Broadly acute. Base: Broadly cuneate. Margin: Entire. Texture, upper and lower surfaces: Smooth, glabrous. Color, upper and lower surfaces: Close to 143C.

*Peduncles*.—Length: About 2.4 cm. Diameter: About 1.5 mm. Strength: Strong. Texture: Smooth, glabrous. Color: Close to 144B.

*Reproductive organs*.—Stamens: Quantity per flower: Five. Filament length: About 1.2 cm. Filament color: Close to NN155C to NN155D. Anther length: About 3 mm. Anther shape: Narrowly oblong. Anther color: Close to 11A. Pollen amount: Moderate. Pollen color: Close to 13A. Pistils: Quantity per flower: One. Pistil length: About 4.5 cm. Stigma shape: Club-shaped. Stigma color: Close to 146C. Style length: About 4.3 cm. Style color: Close to 157D. Ovary color: Close to 144C to 144D.

*Fruits and seeds*.—Fruit and seed development has not been observed on plants of the new *Lonicera*.

Garden performance: Plants of the new *Lonicera* have been observed to have good garden performance and to tolerate rain, wind and to tolerate temperatures ranging from −15° C. to 35° C.

Pathogen & pest resistance: Plants of the new *Lonicera* have not been shown to be resistant to pathogens and pests common to *Lonicera* plants.

It is claimed:

1. A new and distinct *Lonicera* plant named 'Inov205' as illustrated and described.

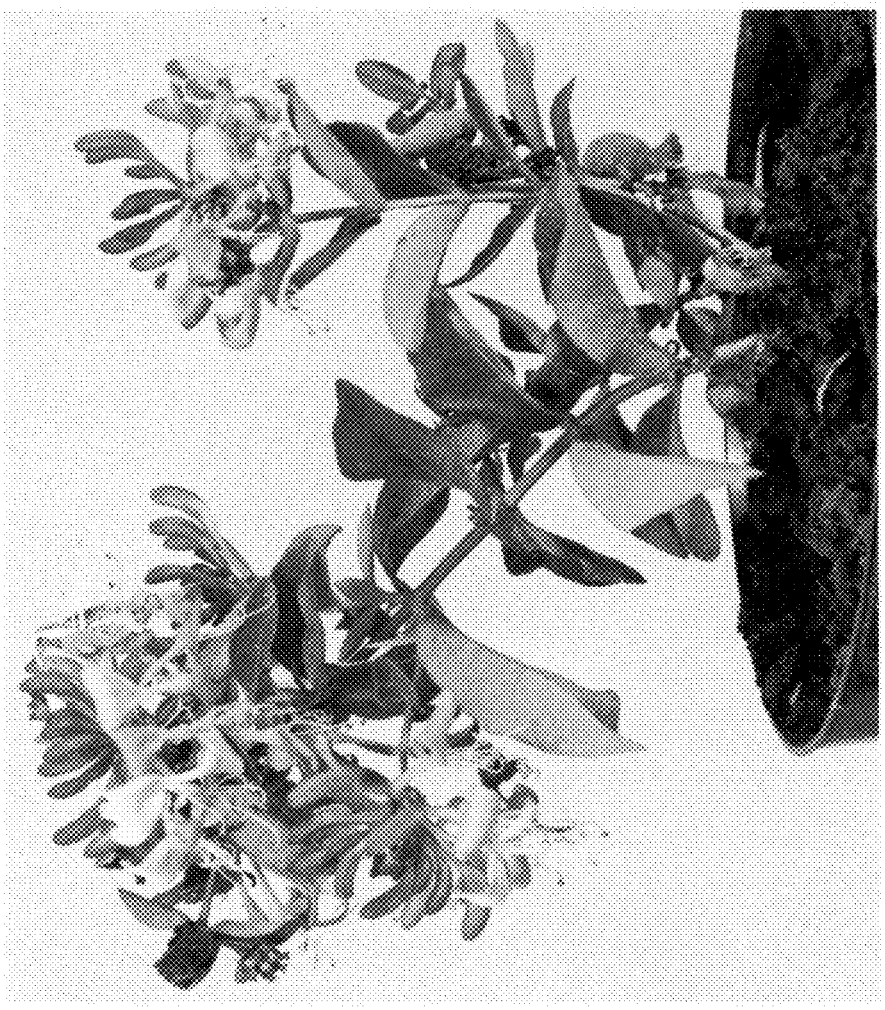

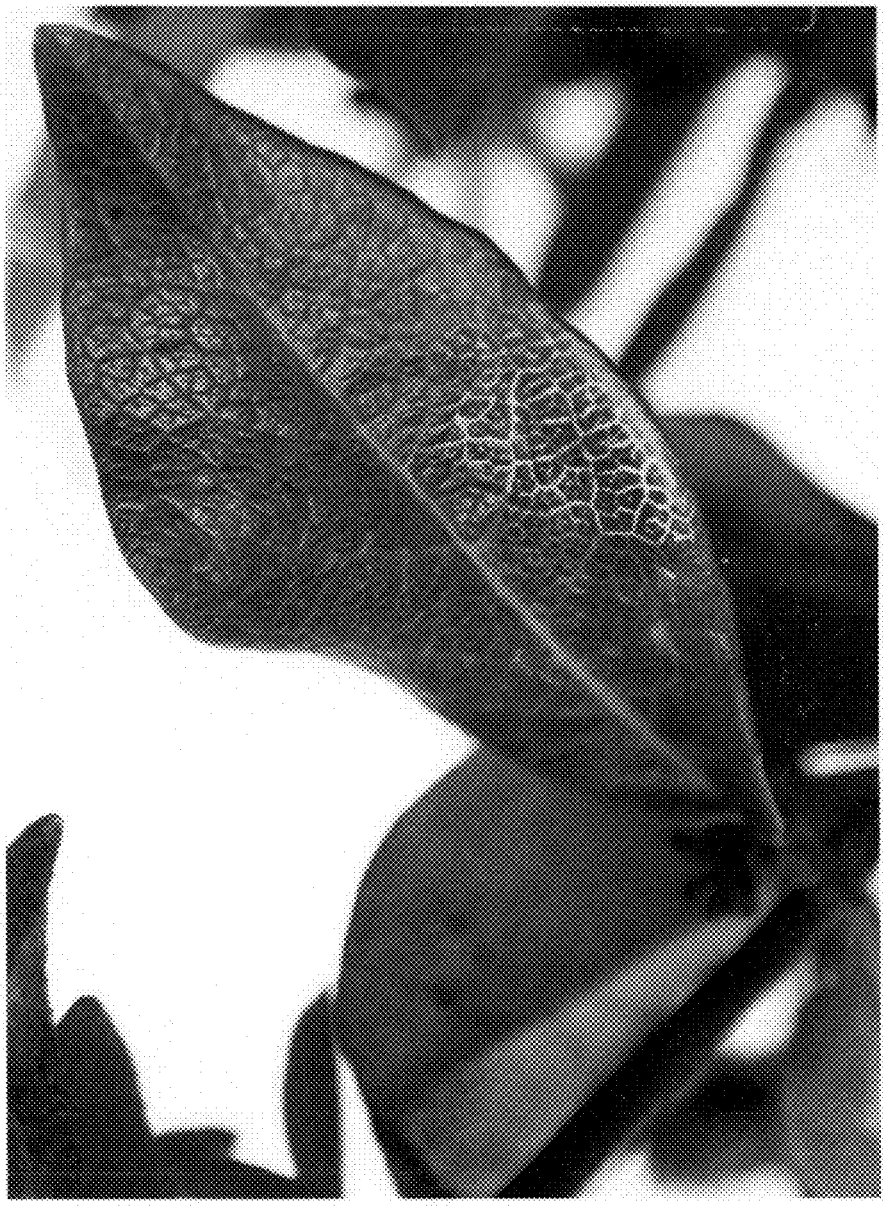

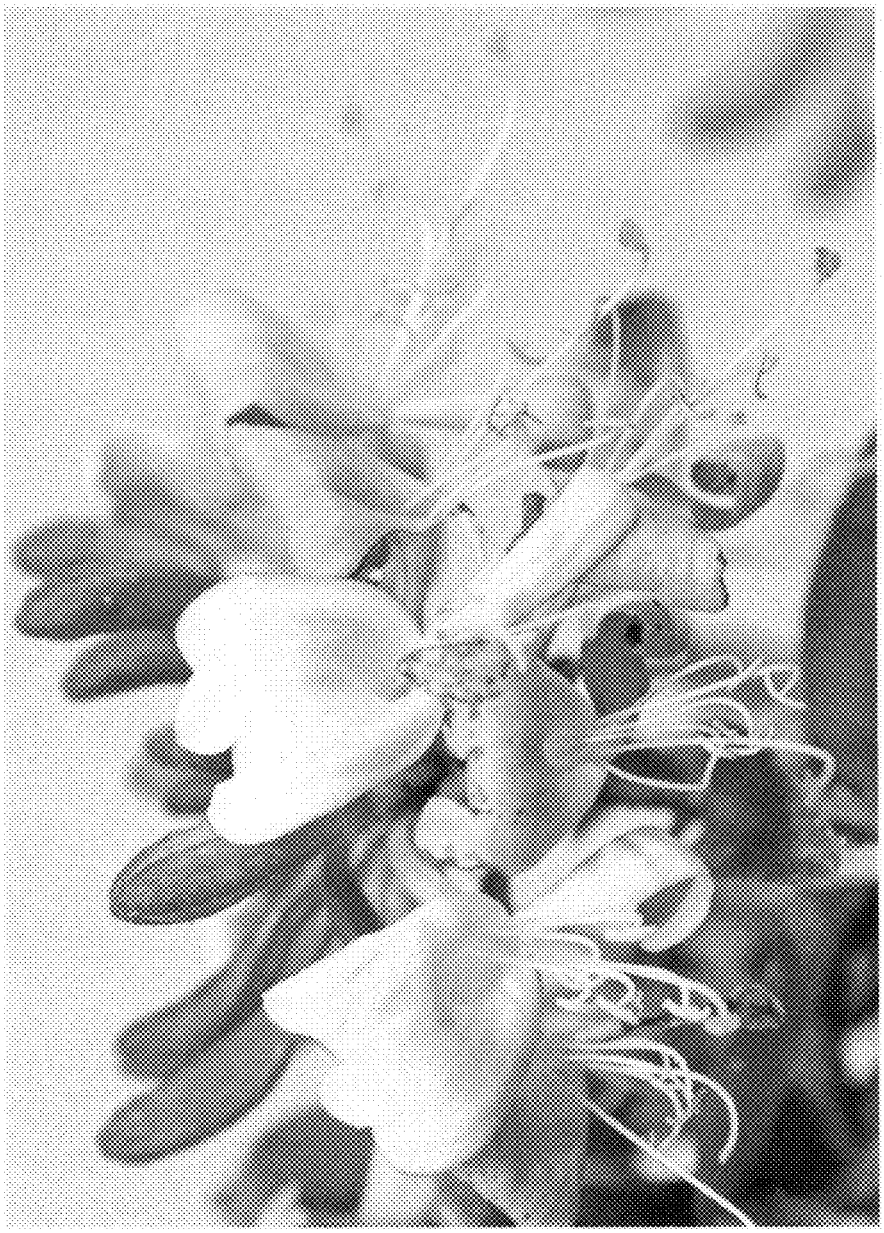

* * * * *